United States Patent [19]

Leitold et al.

[11] Patent Number: 4,769,379
[45] Date of Patent: Sep. 6, 1988

[54] DIANHYDROHEXITE DERIVATIVES, AND THEIR USE AS PHARMACEUTICALS

[75] Inventors: Matyas Leitold, Illertissen; Peter Stoss, Biberach, both of Fed. Rep. of Germany

[73] Assignee: Heinrich Mack Nachf., Illertissen, Fed. Rep. of Germany

[21] Appl. No.: 739,406

[22] Filed: Jul. 2, 1985

[30] Foreign Application Priority Data

Jun. 6, 1984 [DE] Fed. Rep. of Germany ....... 3421072

[51] Int. Cl.$^4$ .................. C07D 473/08; A61K 31/52
[52] U.S. Cl. .................... 514/290; 514/470; 546/277; 549/464; 544/276; 544/277
[58] Field of Search ............ 514/265, 290, 470; 544/276, 277, 268; 546/277; 549/464

[56] References Cited

U.S. PATENT DOCUMENTS 4,535,158 8/1985 Klessing .................... 544/268
4,622,324 11/1986 Klessing et al. ............ 514/265

FOREIGN PATENT DOCUMENTS 3421072 12/1985 Fed. Rep. of Germany .

Primary Examiner—Nicholas S. Rizzo
Attorney, Agent, or Firm—Peter C. Richardson; Lawrence C. Akers; Paul H. Ginsburg

[57] ABSTRACT

Dianhydrohexites of the formula

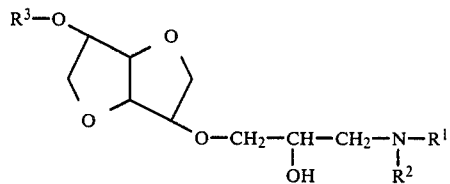

wherein $R^1$ is hydrogen or benzyl, $R_2$ is alkyl or omega-theophyllin-7-yl-alkyl, and $R^1$ and $R_2$ together with the nitrogen atom to which they are attached form a bicyclic group and $R^3$ is hydrogen, acyl, pyridylcarbonyl, nitro or a hydroxylamino group, are formed by an analogous method and used as pharmaceuticals in the treatment of heart and circulatory diseases.

5 Claims, No Drawings

DIANHYDROHEXITE DERIVATIVES, AND THEIR USE AS PHARMACEUTICALS 1,4:3,6-dianhydrohexites, as a class of compounds, have been known for 100 years. A. Fauconnier described the first member as "isomannide" (*Bull. Soc. Chim. France* 41, 119 (1884). This compound and the later known isosorbide, are reported to have diuretic activity; see, for example, *Proc. Soc. Exp. Biol. Med* 119, 39 (1965) and U.S. Pat. No. 2,143,324. In the meantime a series of derivatives has become recognized as pharmacologically active. Of these, isosorbide-2,5-dinitrate has been on the market for many years and isosorbide-5-mononitrate recently, both as coronary therapeutic agents.

DE-OS No. 2,221,080 discloses the mononitrate ester of isosorbide for the treatment of angina pectoris. British Patent No. 1,027,891 describes nicotinic acid esters of 1,4:3,6-dianhydrohexites having vasodilating properties. Muscle-relaxing isohexide ethers are, inter alia disclosed in U.S. Pat. No. 4,169,152. O-substituted 1,4:3,6-dianhydrohexite mononitrates which affect the heart and circulatory system are the subject of DE-OS No. 3,028,289.

In addition to these isohexide derivatives, various desoxy-1,4:3,6-dianhydrohexites with pharmacological activity are known in which the oxygen in the 2- or 5-position may be replaced by an optionally substituted amino group; *J. Indian Chem.* 16 B, 153(1978); DE-OS No. 3,028,272, DE-OS No. 3,028,273; DE-OS No. 3,028,288 and DE-OS No. 3,028,340. Finally, other compounds have been prepared which have no free or substituted hydroxy groups; see especially DE-OS No. 3,109,532 which discloses 1,4:3,6-dianhydro-2,5-dideoxyhexites having hypnotic properties. (See also *Carbohydrate Res.* 85, 259 (1980).

The 1,4:3,6-dianhydrohexite derivatives according to the invention are structurally distinguished from all of the aforementioned compounds in that they contain an N-substituted 3-amino-2-hydroxypropyl group which is attached through an ether bond to the basic structure of the dianhydro sugar alcohol.

It is known that the pharmacophoric functional groups of a large number of so-called beta-receptor blockers exhibit an N-alkylated propanolamine function. The corresponding class is known as "aryloxypropanolamines". By the term "aryl" is generally meant, that the presence of an aromatic or heteroaromatic nucleus is absolutely necessary, especially for the existence of beta-antagonistic activity. (See, e.g. E. Schroder, C. Rufer, R. Schmiechen, "Pharmazeutische Chemie", Thieme Verlag 1982, p. 682 et seq). All pharmaceuticals of this structure introduced into therapy or subjected to clinical testing satisfy this requirement.

Isolated attempts have been made to break with this principle. However, these attempts have as yet had no success. Thus, aliphatic aminohydroxypropanediol ethers are described in J. Med. Chem. 23, 620 (1980), Arch. Pharm. 312, 857 (1979), ibid. 312, 881 (1979) and ibid. 317, 63 (1984). Other examples of this structure are the subject of DE-OS No. 2,558,285, EP No. 37 777 and EP 87 378.

However, none of the afore-described 3-aminopropanediol compounds contains a 1,4:3,6-dianhydrohexite residue.

According to the invention novel compounds are provided which open the possibility, not only of broadening the scope of therapeutic application of isohexide derivates, but also of enriching the class of beta-receptor blockers with hitherto unknown structural variants having superior properties. Surprisingly, the compounds of the invention exhibit a pharmacological activity profile which neither the previously known 1,4:3,6-dianhydrohexites nor the aryloxypropanolamines exhibit. These advantageous pharmacological properties, therefore, present an unforseeable broadening of therapeutic possibilities.

Propanolamines of the stated structure were known to exist as racemates from which, as a rule, only an antipode of the desired pharmacological activity evolved. By the usual methods of synthesis, one only obtains racemic compounds. It is for this reason that all known beta-blockers except Timolol are therapeutically used as racemates. One thus prefers 50% impurity (the "false" enantiomer) to a troublesome racemate splitting. For the preparation of the desired enantiomers from the racemate, expensive known processes are necessary. One of these processes comprises, for example, the conversion into a salt or other derivative with an optically active partner, separation of the resulting diastereomeric salt or other derivative by fractional crystallization, distillation or other suitable way, and subsequent splitting of the salt or derivative to obtain the optically pure isomer. On the other hand, the compounds of this invention form, through the intramolecular combination of a 1,4:3,6-dianhydrohexite residue with a propanolamine group, diastereoisomers ab initio which, if desired, are directly separable without additional chemical reaction. The present invention is therefore directed to novel 1,4:3,6-dianhydrohexite derivatives having the general formula I:

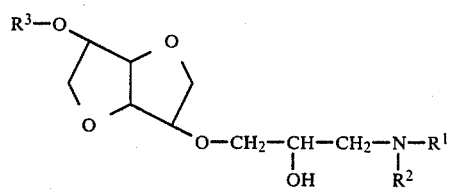

wherein:

$R^1$ is hydrogen or a benzyl group, $R^2$ is a straight- or branched-chain alkyl group with 1–4 carbon atoms or an omega-theophyllin-7-yl-alkyl group wherein the alkyl group may contain 2-3 carbon atoms, or wherein:

$R^1$ and $R^2$ together with the nitrogen atom to which they are attached form the theophyllin-7-yl-group, the theobromine-1-yl group, the adene-9-yl group, optionally mono- or disubstituted at the 6-amino-group, by lower aliphatic or aromatic acyl groups, e.g. acetyl, propionyl, butyryl, isobutyryl, benzoyl or toluyl, the guan-9-yl group, optionally substituted at the 2-amino-group, the 6-chloropurine-9-yl group or the 6-allylmercaptopurine-9-yl group or the 2-amino-6-chloro-purine-9-yl group, optionally substituted at the amino-group, and wherein:

$R^3$ is hydrogen, a straight- or branched-chain saturated or unsaturated acyl radical with 1–20 carbon atoms, a pyridyl-carbonyl radical, nitro or a group having the formula

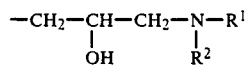

wherein R¹ and R² are as defined above; as well as the salts of such compounds with organic and inorganic acids, preferably physiologically acceptable salts.

1,4:3,6 -dianhydrohexites are bicyclic compounds in the form of two cis-bound tetrahydrofuran rings of which each carries a hydroxyl group. They are prepared by dehydrating the hexites, i.e. hexahydroxy, straight-chain, saturated, aliphatic alcohols having 6 carbon atoms. In addition to the designation "1,4:3,6-dianhydrohexites", the names "1,4:3,6-dianhydrohexitoles", "isohexides" and "isohexitols" are also in use. According to systematic nomenclature, the compounds, as bridged-ring systems, would be called "2,6-dioxabicyclo [3.3.0] octane-4,6-diols" and fused systems "hexahydrofuro[3.2-b]furan-3,6-diols".

The basic compounds of the derivatives discussed here are the following stereoisomers obtained by epimerization of 1,4:3,6-dianhydrohexites, viz.: 1,4:3,6-dianhydro-L-idite (isoidide) having the following structure,

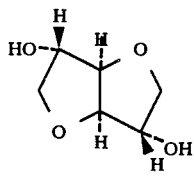

wherein the OH groups in the 2- and 5-positions exhibit exo-configuration or 1,4:3,6-dianhydro-D-glucite (1,4:3,6 dianhydro-D-sorbite, isosorbide) having the following structure,

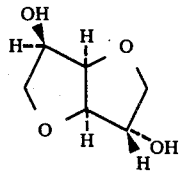

which shows a 2-exo as well as a 5-endo OH group and whose O-derivative, in the case of non-identical subsituents, exists in two isomeric forms or 1,4:3,6-dianhydro-D-mannite (isomannide) having the following structure:

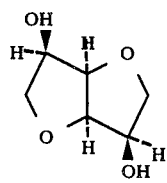

which has two endo OH groups.

In contrast to the glucite derivatives, in the idite and mannite derivatives there is no difference between substitution in the 2- and in the 5-position. A short summary of the stereochemistry of the 1,4:3,6-dianhydrohexites is given by J. A. Mills in *Advances in Carbohydrate Chemistry* 10, 1–53 (1955) and L. Hough and A. C. Richardson in "Rodd's Chemistry of Carbon Compounds", 2d. ed., Vol. 1, F, Elsevier, 1967, pp. 51–55.

1,4:3,6 -dianhydrohexites have four chiral centers at carbon atoms 2,3,4 and 5. The starting materials for the preparation of the compounds of this invention are in the optically pure form, as the L-isoidide, the D-isosorbide and the D-isomannide. They are obtainable from the corresponding, naturally occurring, optically active sugar alcohols. The N-substituted 3-amino-2-propanol side-chain

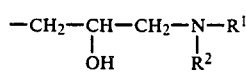

in the compounds of this invention have in the C-2 likewise an asymmetric carbon atom. For this reason, the compounds of this invention in general Formula I are in diastereoisomeric form. The diastereoisomeric mixtures and the separated, optically pure components are also part of the present invention.

Compounds of the invention are therefore 1,4:3,6-dianhydro-L-idite derivatives having the general Formula II

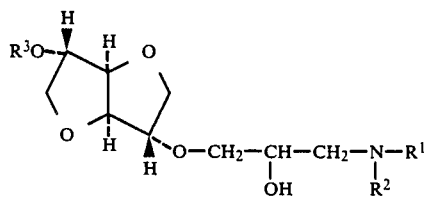

and salts thereof, wherein R¹, R² and R³ are as defined above, 1,4:3,6-dianhydro-D-glycite derivatives having the general Formulae III and IV

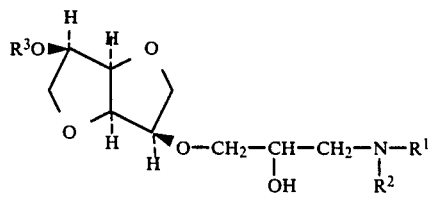

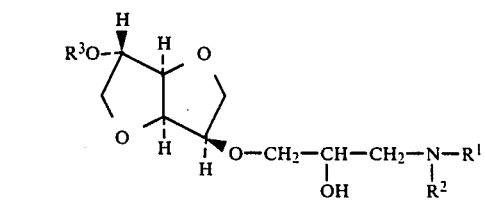

and salts thereof, wherein R¹, R² and R³ are as defined above, 1,4:3,6-dianhydro-D-mannite derivatives having the general Formula V

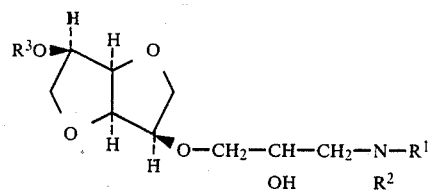      V wherein $R^1$, $R^2$ and $R^3$ are as defined above.

The compounds of the present invention may be prepared by processes known per se. One of the processes for preparation of compounds of Formula I is characterized in that a (2,3-epoxypropyl)-1,4:3,6-dianhydrohexite having the general Formula VI

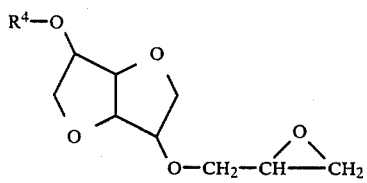   VI wherein $R^4$ is hydrogen, a straight- or branched-chain saturated or unsaturated acyl radical having 1-20 carbon atoms, a pyridylcarbonyl radical, an $NO_2$ group or a 2,3-epoxypropyl radical having the formula

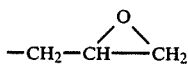

is reacted, in known manner, with a compound having the general Formula VII

wherein $R^1$ and $R^2$ are as defined above. The reaction product having general Formula I may be converted into a salt of an inorganic or an organic acid, preferably a pharmaceutically acceptable acid.

If by this conversion a diastereoisomeric mixture is used initially, the final product is also a diastereoisomeric mixture. If an optically pure isomer is used as reaction partner, a pure diastereoisomer is obtained. Diastereoisomeric mixtures may be separated into pure components by known separation techniques.

The reaction of epoxides of the general Formula VI with compounds of the general Formula VII may proceed without a solvent or with a suitable solvent which is inert under the reaction conditions. Such solvents are water; lower alcohols such as methanol, ethanol, 1-propanol, 2-propanol and butanol; ethers such as diethyl ether, diisopropyl ether, dibutyl ether, ethyleneglycol mono- and dimethyl ethers and diethyl ethers, tetrahydrofuran and dioxane; dimethyl formamide (DMF) and dimethyl sulfoxide (DMSO). The reaction temperature may be between 0° and 200° C., usually at about room temperature up to the boiling point of compound VII or the solvent used. The mol ratios of the reaction partners VI and VII may be chosen as desired and are in the range of 1:1 to 1:100. Reaction times are in the range of 0.5 to 24 hours.

At the end of the conversion, the reaction products of general Formula I are recovered in the usual manner, purified and, optionally, converted to the salt of an inorganic or an organic acid, preferably to a pharmaceutically acceptable salt. Examples of such salts are chlorides, bromides, nitrates, sulfates, phosphates, acetates, oxalates, maleates, fumarates, tartrates, lactates, maleinates, malonates, citrates, salicylates, methanesulfonates, benzenesulfonates, p-toluenesulfonates and naphthalenesulfonates.

These or other salts of the new compounds, e.g. picrates, may also purify the free bases by converting the free base to a salt, separating the salt and, optionally, recrystallizing or otherwise purifying the salt and liberating the free base.

Compounds of general Formula VI, wherein $R^4$ is as previously defined, are obtainable in known manner from 1,4:3,6-dianhydrohexites having the general Formula VIII

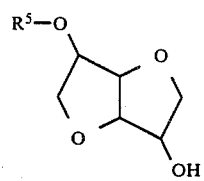   VIII wherein $R^5$ is hydrogen, a straight-chain or branched-chain, saturated or unsaturated acyl radical having 1-20 carbon atoms, a pyridylcarbonyl radical or an $NO_2$ group, (a) by reaction with an epihalohydrin having the Formula

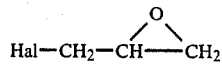   IX wherein Hal is a halogen radical, expecially chlorine, bromine or iodine, in the presence of a base or (b) by reaction with an alkyl halide having Formula X

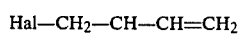   X wherein Hal is a halogen radical, especially chlorine, bromine or iodine, in the presence of a base, whereby, first, compounds of general Formula XI are formed:

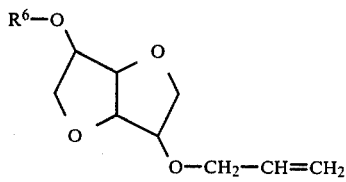   XI wherein $R^6$ is hydrogen, a straight-chain or branched-chain, saturated or unsaturated acyl radical having 1-20 carbon atoms, a pyridylcarbonyl radical, an $NO_2$ group or an allyl radical having the Formula $-CH_2-CH=CH_2$ and subsequent oxidation of compounds XI to compounds according to general Formula VI.

For the epoxidation of compounds XI, all compounds available to the person skilled in the art can be used, e.g. peracetic acid, perbenzoic acid, m-chloroperbenzoic acid, monoperphthalic acid and others. For methods and reaction conditions, see, for example, Houben-Weyl VI/3, page 385 et seq.

Use of racemic epihalohydrin of general Formula IX as reaction partner according to (a) yields a diastereoisometric mixture. The mixture can be resolved into its components, if necessary, by known separation techniques. When a pure enantiomer of epihalohydrin is used in the above reaction, one of the possible diastereoisomers is obtained depending on the absolute configuration of the enantiomer used.

The required oxidation of allyl compounds XI according to (b) creates a new chirality center. Thus, the 2,3-epoxypropyl derivatives obtained in this way appear as diastereoisomeric mixtures which may be resolved into the pure isomers.

The reaction of VIII with IX or X can be carried out without solvents or with suitable solvents which are inert under the reaction conditions. As such the following may be used: acetone, methyl-ethyl ketone, benzene, toluene, xylene, ethylene glycol dimethyl and diethyl ether, dioxane, tetrahydrofuran, DMF and DMSO.

As bases for these reactions, one may use sodium hydride, potassium hydride, sodium hydroxide, potassium hydroxide, sodium carbonate, potassium carbonate, or potassium tert-butylate. Reaction temperatures may be between 0° C. and 180° C., usually from about room temperature to the boiling point of the epichlorhydrin, the allyl halide or the solvent. The mol ratio of VIII to IX or X may be chosen as desired from 1:1 to 1:100. The reaction times are in the range of 0.5 to 24 hours.

If compounds of the general Formula VIII in which $R^5$ is hydrogen are used as starting materials in reactions according to (a) and (b), mono- and disubstituted products may be formed. In the case of 1,4:3,6-dianhydro-D-glucites (isosorbide) two isomeric monosubstitution products are to be expected. By proper choice of mol ratios and reaction conditions the reaction may be steered in the desired direction. Also, mixtures of mono- and disubstituted products, as well as isomeric 2- and 5-substituted isosorbides, may be separated by known methods, e.g. crystallrzation, distillation, extraction or chromatography.

Compounds of general Formula VI wherein $R^4$ is as defined above, except hydrogen and the 2,3-epoxypropyl radical, are obtainable from compounds of general Formula VI, and, where $R^4$ is hydrogen, by reaction with straight chain or branched, saturated or unsaturated acylhalides having 1-20 carbon atoms or the corresponding pyridylcarbonyl halides and with nitric acid. These conversions proceed in ways known per se.

In like manner, compounds of general Formula XI, wherein $R^6$ is as defined above except hydrogen and an alkyl radical, may be prepared by reacting compounds of general Formula XI wherein $R^6$ is hydrogen with straight or branched, saturated or unsaturated acyl halides having 1-20 carbon atoms or the corresponding carboxylic anhydrides, with pyridylcarbonyl chlorides and with nitric acid. These reactions proceed in known manner and according to usual methods.

2,5-Bis-(2,3-epoxypropyl)-ethers of the isosorbides, isomannides and isoidides are described in U.S. Pat. No. 3,272,845. Mono-epoxypropyl-1,4:3,6-dianhydrohexites and all derivatives thereof are novel intermediates.

Examples of compounds of general Formula VI which are new intermediates according to this invention are:
2-(2,3-epoxypropyl)-isosorbide
5-(2,3-epoxypropyl)-isosorbide
2-(2,3-epoxypropyl)-isomannide
2-(2,3-epoxypropyl)-isoidide
2-(2,3-epoxypropyl)-isosorbide-5-nitrate
5-(2,3-epoxypropyl)-isosorbide-2-nitrate
2-(2,3-epoxypropyl)-isomannide-5-nitrate
2-(2,3-epoxypropyl)-isoidide-5-nitrate
2-(2,3-epoxypropyl)-isosorbide-5-nicotinate
5-(2,3-epoxypropyl)-isosorbide-2-nicotinate
2-(2,3-epoxypropyl)-isosorbide-5-isonicotinate
5-(2,3-epoxypropyl)-isosorbide-2-isonicotinate
2-(2,3-epoxypropyl)-isomannide-5-nicotinate
2-(2,3-epoxypropyl)-isomannide-5-isonicotinate
2-(2,3-epoxypropyl)-isoidide-5-nicotinate
2-(2,3-epoxypropyl)-isoidide-5-isonicotinate
2-(2,3-epoxypropyl)-isosorbide-5-acylate
5-(2,3-epoxypropyl)-isosorbide-2-acylate
2-(2,3-epoxypropyl)-isomannide-5-acelyate
2-(2,3-epoxypropyl)-isoidide-5-acelyate In the last four compounds, the expression "acylate" refers to straight or branched, saturated or unsaturated carboxylic acid radicals having 1-20 carbon atoms. Examples are formate, acetate, propionate, acrylate, butyrate, isobutyrate, pivaloate (trimethyl acetate), caprylate (octanoate), decanoate, undecenoylate, stearate and arachinate.

The preparation of 2,5-diallyl-isosorbide and 2,5-diallylisommannide is described in J. Chem. Soc., 1947, 1405, and in J. Chem. Soc., 1950, 591. In the latter reference 2-allyl-isomannide, 2-allyl-isomannide-5-acetate and the unresolved mixtures of 2- and 5-allyl-isosorbide and allyl-isosorbide acetates are also mentioned. Allyl compounds of the isoidides as well as all other allyl compounds of the 1,4:3,6 -dianhydrohexite derivatives XI used according to this invention are also novel.

Examples of compounds of general Formula XI which are intermediates according to this invention are:
2-Allyl-isosorbide
5-Allyl-isosorbide
2-Allyl-isomannide
2-Allyl-isoidide
5-Allyl-isosorbide-5-nitrate
2-Allyl-isosorbide-2-nitrate
2-Allyl-isomannide-5-nitrate
2-Allyl-isoidide-5-nitrate
2-Allyl-isosorbide-5-nicotinate
5-Allyl-isosorbide-2-nicotinate
2-Allyl-isosorbide-5-isonicotinate
5-Allyl-isosorbide-2-isonicotinate
2-Allyl-isomannide-5-nicotinate
2-Allyl-isomannide-5-isonicotinate
2-Allyl-isoidide-5-nicotinate
2-Allyl-isoidide-5-isonicotinate
2-Allyl-isosorbide-5-acylate
5-Allyl-isosorbide-2-acylate
2-Allyl-isommanide-5-acylate
2-Allyl-isoidide-5-acylate In the case of the last four compounds, the expression "acylate" refers to a straight or branched, saturated or unsaturated acid radical having 1-20 carbon atoms. Examples are formate, acetate, propionate, acrylate, butyrate, isobutyrate, pivaloate, caprylate, decanoate, undecanoate, stearate and arachinate.

The compounds according to the invention, surprisingly, are distinguished by a broad spectrum of pharmacological activity and, therefore, represent valuable pharmaceuticals. They possess beta-sympatholytic, blood-pressure-depressing, negative inotropes and heart-frequency-depressing activity. They exhibit spasmolytic, broncholytic and antitussive properties and also effect an improvement of the peripheral and central blood circulation. They may therefore on the one hand be used for prophylaxis and treatment of various diseases of the heart and circulation and on the other hand as spasmolytics, broncholytics, antitussives and stimulants. They therefore have properties not hitherto known for 1,4:3,6-dianhydrohexite derivatives.

Specific examples of compounds according to the invention are:
2-(2-hydroxy-3-isopropylaminopropyl)-isosorbide;
2-(2-hydroxy-3-tert.-butylaminopropyl)-isosorbide;
2-(2-hydroxy-3-tert.-butylaminopropyl)-isosorbide-5-nitrate
5-(2-hydroxy-3-tert.-butylaminopropyl)-isosorbide-2-nitrate
5-(2-hydroxy-3-tert.-butylaminopropyl)-isosorbide;
5-(2-hydroxy-3-isopropylaminopropyl)-isosorbide;
2,5-bis-(2-hydroxy-3-tert.-butylaminopropyl)-isosorbide;
2,5-bis-(2-hydroxy-3-isopropylaminopropyl)-isosorbide;
2-(2-hydroxy-3-isopropylaminopropyl)-isosorbide-5-nitrate;
2-(2-hydroxy-3-isopropylamiopropyl)-isomannide;
2-(2-hydroxy-3-isopropylaminopropyl)-isomannide-5-nitrate;
2,5-bis-(2-hydroxy-3-isopropylaminopropyl)-isomannide;
2-(2-hydroxy-3-isopropylaminopropyl)-isoidide;
2-(2-hydroxy-3-isopropylaminopropyl)-isoidide-5-nitrate;
2-((2-hydroxy-3-isopropylaminopropyl)-isosorbide-5-stearate;
2-(2-hydroxy-3-isopropylaminopropyl)-isosorbide-5-isobutyrate;
2-(2-hydroxy-3-isopropylaminopropyl)-isosorbide-5-pivaloate;
2-(2-hydroxy-3-isopropylaminopropyl)-isosorbide-5-caprinate;
2-(2-hydroxy-3-isopropylaminopropyl)-isosorbide-5-acetate;
2-(2-hydroxy-3-isopropylaminopropyl)-isosorbide-5-undecylenate
2-[2-hydroxy-3-(7-theophyllinyl)-propyl]-isosorbide;
2-[2-hydroxy-3-(7-theophyllinyl)-propyl]-isosorbide-5-nitrate
5-[2-hydroxy-3-(7-theophyllinyl)-propyl]-isosorbide-2-nitrate
bis-2,5[2-hydroxy-3-(7-theophyllinyl)-propyl]-isosorbide;
2-[2-hydroxy-3-(1-theobrominyl)-propyl]-isosorbide;
5-[3-[N-benzyl-N-(2-(7-theophyllinyl)-ethylamino)]-2-hydroxy-propyl]-isosorbide;
2-[3-[N-benzyl-N-(2-(7-theophyllinyl)-ethylamino)]-2-hydroxypropyl]-isosorbide;
5-[3-[2-(7-theophyllinyl)-ethylamino]-2-hydroxypropyl]-isosorbide;
5-[3-[N-benzyl-N-(2-(7-theophyllinyl)-ethylamino)]-2hydroxypropyl]-isosorbid-2-nitrate
2-[3-[N-benzyl-N-(3-(7-theophyllinyl)-propylamino)]-2hydroxypropyl]-isosorbide;
2-[3-[3-(7-theophyllinyl)-propylamino]-2-hydroxypropyl]-isosorbide;
2-[3-[2-(7-theophyllinyl)-ethylamino]-2-hydroxypropyl]-isosorbide;
2-[3-[N-benzyl-N-(2-(7-theophyllinyl)-propylamino)]-2hydroxypropyl]-isosorbide-5-nitrate;
2-[3-[N-benzyl-N-(3-(7-theophyllinyl)-propyl)-amino]-2-hydroxypropyl]-isomannide;
2-[3-[3-(7-theophyllinyl)-propylamino]-2-hyroxypropyl]-isomannide;
5-[3-[2-(7-theophyllinyl)-ethylamino]-2-hydroxypropyl]-isosorbide-2-nitrate;
2-[3-[3-(7-theophyllinyl)-propylamino]-2-hydroxypropyl]-isosorbide-5-nitrate;
2-[3-($N^6$-benzoyl-9-adenyl)-2-hydroxypropyl]-isosorbide;
2-[3-(9-adenyl)-2-hydroxypropyl]-isosorbide;
bis-2,5-[3-[N-benzyl-N-(2-(7-theophyllinyl)-ethyl)amino]-2-hydroxypropyl]-isomannide;
bis-2,5-[3-[2-(7-theophyllinyl)-ethylamino]-2-hydroxypropyl]-isomannide;
2-[3-(9-(6-methylmercaptopurinyl))-2-hydroxypropyl]-isosorbide.

An aspect of the invention is also the use of compounds of general Formula I and salts thereof as pharmaceuticals. Such pharmaceuticals may contain compounds of the invention or salts thereof in amounts of 0.1 to 99.9%. Dosage may be as desired within the range of 1 to 500 mg.

All suitable formulation known in the art can be used, e.g. suppositories, powders, granulates, tablets, capsules, suspensions, liquids, injectables and transdermal systems. For the preparation of pharmaceutical compositions, solid, semi-solid or liquid carrier material or diluents can be used. This includes corrigents, binders, lubricants, emulsifiers etc. Examples are: starch, such as potato and cereal starch, sugars, such as lactose, sucrose, glucose, mannitol, sorbitol, cellulose, such as crystalline cellulose, methylcellulose, calcium carboxymethyl cellulose, carboxymethyl cellulose, and hydroxypropyl cellulose, inorganic materials such as potassium phosphate, calcium sulfate, calcium carbonate and talcum, gelatine, gum arabic, polyvinylpyrrolidone, suface-active substances such as fatty acid glycerides, fatty acid sorbitan esters, fatty acid esters of sucrose and polyglycerol and others.

Examples of pharmaceutical formulations utilizing compounds of the invention are:

| Tablets: | |
|---|---|
| Composition | mg/tablet |
| Compound of invention | 3 |
| Microcrystalline cellulose | 25 |
| Lactose | 17 |
| Calcium carboxymethylcellulose | 4.5 |
| Magnesium stearate | 0.5 |

The above ingredients are sieved, thoroughly and carefully mixed, and pressed in a suitable tablet press.

| Capsules: | |
|---|---|
| Composition | mg/capsule |
| Compound according to invention | 10 |
| Lactose | 40 |
| Microcrystalline cellulose | 30 |
| Talcum | 10 |

The above ingredients are sieved, carefully and thoroughly mixed, and placed in hard gelatine capsules by use of a suitable capsule-filling machine.

An aspect of the invention is also the use of the compounds of the invention for the treatment of heart and circulatory diseases.

The following examples serve to illustrate the invention. Unless otherwise noted, the compounds specified in the examples were used as diastereoisomeric mixtures.

EXAMPLE 1

2-(2-hydroxy-3-isopropylaminopropyl)isosorbide (a) 2-allyl-isosorbide, 5-allyl-isosorbide, 2,5-diallyl-isosorbide; 450 g isosorbide, 600 g potassium carbonate and 400 ml allyl bromide are heated in 1 l toluene for 24 hours under reflux. After cooling, the product is filtered from the inorganic salts, washed with 0.5 l toluene and concentrated. The residue is taken up in 1 l water and extracted 3 times, each time with 200 ml ether. The combined ether phases are counterextracted with 200 ml water, dried, concentrated and vacuum-distilled in a column. Obtained is 90 g 2,5-diallyl isosorbide, b.p. (0.1): 84° C.

The combined water phases are saturated with sodium chloride and twice shaken with 1 l dichloromethane each time. After drying and concentration of the combined organic phases, the residue is vacuum-fractionated in a column. One obtains 180 g 2-allyl-isosorbide, b.p. (0.1): 72° C. m.p. 35° C. from diethylether, 20 g mixed fraction, b.p. (0.1): 72°–112° 112 g 5-allyl-isosorbide, b.p. (0.1): 112° C.;

(b) 2-(2,3-epoxypropyl)-isosorbide: 18.6 g 2-allyl-isosorbide and 25 g 3-chloroperbenzoic acid is stirred in 100 ml chloroform for 24 hours at room temperature.

Thereafter the precipitated 3-chloroperbenzoic acid is suction-filtered and the filtrate concentrated. The residue is taken up in water and extracted with ether. The residue is taken up in water and extracted with ether. The residue remaining after concentration of the water phase can either be distilled or recrystallized from ethyl acetate/ether b.p. (0.1): 108° C.; m.p. 74° C. [alpha]$_D^{20}$+53.9 (c=0.892, methanol).

By repeated recrystallization from methyl-ethyl ketone, one obtains an isomer with m.p. 88°–90° C., [alpha]$_D^{20}$+66.1 (c=1.022, methanol).

From the mother liquor, the other isomer can be isolated. M.p. 60°–62° (from ethyl acetate/ether), [alpha]$_D^{20}$+40.4 (c=0.904, methanol).

(c) 2-(2-hydroxy-3-isopropylaminopropyl)-isosorbide: 20.2 g 2-(2,3-epoxypropyl) isosorbide (isomeric mixture) is heated under reflux with 17.8 g isopropylamine in 500 ml ethanol for 3 hours. Thereafter the solvent and excess amine are removed in a rotary vaporizer in vacuo. The solid residue is recrystallized from diisopropyl ether. Yield: 20,1 g (77%), m.p. 65°–67° C., [alpha]$_D^{20}$+38.5 (c=0.80, methanol).

The two diastereoisomeric forms are obtainable by resolution of this diastereoisomeric mixture as well as by starting with isomerically pure epoxides. M.P. 83°–84° C. (from carbon tetrachloride/ether), [alpha]$_D^{20}$+36.7 (c=0.90, methanol). M.P. 103°–105° C. (from acetone/ether), [alpha]$_D^{20}$+42.8 (c=0.841, methanol).

EXAMPLE 2

2-(2-hydroxy-3-tert.-butylaminopropyl)-isosorbide

The preparation is analogous to that of Example 1c, from 2-(2,3-epoxypropyl)-isosorbide and tert.butylamine. M.P. 90°–92° C. (from carbon tetrachloride), [alpha]$_D^{20}$+170.8 (c=0.612, acetone).

EXAMPLE 3

2-(2-hydroxy-3-tert.-butylaminopropyl)-isosorbide-5-nitrate (a) 2-allyl-isosorbide-5-nitrate: 191 g isosorbide-5-nitrate, 200 g potassium carbonate and 150 ml allylbromide are heated in 300 ml toluene for 24 hours under reflux. After cooling, filtration from the inorganic salts and washing with toluene are effected, and the filtrate is extracted several times with water. The organic phase is concentrated in vacuo, and 160 g 2-allyl-isosorbide-5-nitrate remains as an oily, crude product which is used in the following conversion.

(b) 2-(2,3-epoxypropyl)-isosorbide-5-nitrate: 0.1 mole raw 2-allyl-isosorbide-5-nitrate is stirred with 25 g 3-chloroperbenzoic acid in 100 ml chloroform for 24 hours at room temperature. Then one extracts with 2N sodium hydroxide and concentrates the organic phase. The oily product is used in the following stage without further purification.

(c) 2-(2-hydroxy-3-tert. aminopropyl)isosorbide-5-nitrate;

0.1 mole crude 2-(2,3-epoxypropyl)-isosorbide-5-nitrate is allowed to stand for 24 hours with 0.3 mole tert.-butylamine and 10 ml methanol. Thereafter one concentrates in a rotary vaporizer in vacuo. The oily residue is converted with fumaric acid into the semifumarate. M.P. 167°–168° C. (from ethanol), [alpha]$_D^{20}$+72.3 (c=0.775, H$_2$O).

EXAMPLE 4

5-(2-hydroxy-3-tert. butylaminopropyl)-isosorbide-2nitrate (a) 5-allyl-isosorbide-2-nitrate: From 191 g isosorbide-2-nitrate one obtains, analogous to Example 3a, 145 g oily, crude product which is used further in this form.

(b) 5-(2,3-epoxypropyl)-isosorbide-2-nitrate: Analogous to Example 3(b), an oily product, sufficiently pure for the subsequent conversion, is obtained.

(c) 5-(2-hydroxy-3-tert. butylaminopropyl)-isosorbide-2-nitrate: The preparation is analogous to that in Example 3(c). Maleate: m.p. 118°–120° C. (from 2-propanol) [alpha]$_D^{20}$+37.6 (c=0.732, H$_2$O).

EXAMPLE 5

5-(2-hydroxy-3-tert.-butylaminopropyl)-isosorbide (a) 5-(2,3-epoxypropyl)-isosorbide: By conversion of 5-allyl-isosorbide with 3-chloroperbenzoic acid, analogous to Example 1(b), one obtains the title compound in the form of a colorless oil.

(b) 5-(2-hydroxy-3-tert.-butylaminopropyl)-isosorbide: Maleate: m.p. 139°–142° C. (from ethanol), [alpha]$_D^{20}$+35.8 (c=0.838, H$_2$O).

EXAMPLE 6

5-(2-hydroxy-3-isopropylaminopropyl)-isosorbide

Oxalate: 0.5 H$_2$O: m.p. 54° C. (from 2-propanol), [alpha]$_D^{20}$+38.9 (c=0.757, H$_2$O).

EXAMPLE 7

2,5-bis-(2-hydroxy-3-tert. butylaminopropyl)-isosorbide (a) 2,5-bis-(2,3-epoxypropyl)-isosorbide: Preparation according to U.S. Pat. No. 3,272,845, b.p. (0.1): 147° C. [alpha]$_D^{20}$+85.3 (c=7.28, methanol). A product obtained from 2,5-diallylisosorbide (Example 1a) by conversion with 3-chloroperbenzoic acid has identical properties.

(b) 2,5-bis-(2-hydroxy-3-tert.-butylaminopropyl)-isosorbide: Oxalate: m.p. 234°–236° C. (from methanol-/acetone), $[alpha]_D^{20}+27.6$ (c=0.797, $H_2O$).

EXAMPLE 8

2,5-bis-(2-hydroxy-3-isopropylaminopropyl)-isosorbide Dioxalate: m.p. 143°–145° C. (from methanol/acetone), $[alpha]_D^{20}+26.4$ (c=1.16, $H_2O$).

EXAMPLE 9

2-(2-hydroxy-3-isopropylaminopropyl)-iosorbide-5-nitrate M.P. 76°–78° C. (from ether), $[alpha]_D^{20}+44.2$ (c=0.775, $H_2O$).

EXAMPLE 10

2-(2-hydroxy-3-isopropylaminopropyl)-isomannide (a) 2-allyl-isomannide, 2,5-diallyl-isomannide: 450 g isomannide is converted, analogous to Example 1(a), with allylbromide. One obtains 80 g 2,5-diallyl-isomannide, b.p. (0.1): 94°–100° C.; and 310 g 2-allyl-isomannide, b.p. (0.1): 85°–90° C.

(b) 2-(2,3-epoxypropyl)-isomannide: The preparation proceeds analogous to Example 1(b), by epoxidation of 2-allyl-isomannide with 3-chloroperbenzoic acid. The oily, crude product obtained is used in the next stage without further purification.

(c) 2-(2-hyroxy-3-isopropylaminopropyl)-isomannide: Analogous to Example 1(c). M.p. 80°–82° C. (from ethyl acetate), $[alpha]_D^{20}+101.4$ (c=0.764, $H_2O$).

EXAMPLE 11

2-(2-hydroxy-3-isopropylaminopropyl)-isomannide-5-nitrate (a) 2-allyl-isomannide-5-nitrate: To a mixture of 13 g 65% nitric acid and 45 ml acetic anhydride is added dropwise, with stirring, at 0°–5° C., 18.6 g 2-allyl-isomannide. After 15 minutes at this temperature, the mixture is poured into water and extracted with dichloromethane. The organic phase is concentrated in a rotary evaporator. 23 g oily 2-allyl-isomannide-5-nitrate remains as a residue.

(b) 2-(2,3-epoxypropyl)-isomannide-5-nitrate: The product obtained in (a) is converted with 3-chloroperbenzoic acid analogous to Example 1(b). One obtains an oily, crude product which is used in this form in the following stage.

(c) 2-(2-hydroxy-3-isopropylaminopropyl)-isomannide-5-nitrate: Analogous to Example 1(c), from above crude epoxide and isopropylamine. Oxalate: M.p. 81°–82° C. (acetone/ether), $[alpha]_D^{20}+157$ (c=0.793, methanol).

EXAMPLE 12

2,5-bis-(2-hydroxy-3-isopropylaminopropyl)-isomannide (a) 2,5-bis-(2,3-epoxypropyl)-isomannide: Analogous to Example 7(a) from 2,5-diallylisomannide and 3-chloroperbenzoic acid. The oily, crude product is suitable for the further conversion.

(b) 2,5-bis-(2-hydroxy-3-isopropylaminopropyl)-isomannide: Dioxalate: 0.5 $H_2O$: m.p. 124°–128° C. (from methanol) $[alpha]_D^{20}+64.3$ (c=0.848, $H_2O$).

EXAMPLE 13

2-(2-hydroxy-3-isopropylaminopropyl)-isoidide (a) 2-allyl-isoidide, 2,5-diallyl-isoidide; According to Example 1(a), by conversion of isoidide with allylbromide, 2-allyl-isoidide is obtained as the major product. B.p. (0.1): 110°–111° C. 2,5-diallyl-isoidide is obtained in smaller amount.

(b) 2-(2,3-epoxypropyl)-isoidide: Obtained as an oily, crude product analogously to Example 1(b) and reacted further in this form.

(c) 2-(2-hydroxy-3-isopropylaminopropyl)-isoidide: Oxalate: 0.5 $H_2O$: m.p. 75°–80° C. (from acetonitrile), $[alpha]_D^{20}+18.05$ (c=0.637, $H_2O$).

EXAMPLE 14

2-(2-hydroxy-3-Isopropylaminopropyl)-isoidide-5-nitrate (a) 2-allyl-isoidide-5-nitrate: From 2-allyl-isoidide and nitric acid, analogous to Example 11(a), one obtains an oily, crude product, which is further converted without further purification.

(b) 2-(2,3-epoxypropyl-isoidide)-5-nitrate: Analogous to 11(b), oily, crude product.

(c) 2-(2-hydroxy-3-isopropylaminopropyl)-isoidide-5-nitrate: Oxalate: m.p. 117°–118° C. (from ethanol), $[alpha]_D^{20}+30.1$ (c=0.747, methanol).

EXAMPLE 15

2-(2-hydroxy-3-isopropylaminopropyl)-isosorbide-5-stearate (a) 2-allyl-isosorbide-5-stearate: A mixture of 18.6 g 2-allyl-isosorbide, 29.8 g methyl stearate and 0.1 g sodium methylate is heated for 2 hours at 100° C. in a water-stream vacuum. Then the product is distilled in vacuo. B.p. (0.05):210° C.

(b) 2-(2,3-epoxypropyl)-isosorbide-5-stearate: By conversion of the foregoing compound with m-chloroperbenzoic acid in chloroform and the usual processing. The product is obtained in oily form and directly further processed.

(c) 2-(2-hydroxy-3-isopropylaminopropyl)-isosorbide-5-stearate: Reaction of the foregoing epoxide with isopropylamine yields the desired product. Tartrate 2 $H_2O$: m.p. 58°–60° C. (from ethyl acetate), $[alpha]_D^{20}+32.9$ (c=0.849, $H_2O$).

EXAMPLE 16

2-(2-hydroxy-3-isopropylaminopropyl-isosorbide-5-isobutyrate (a) 2-allyl-isosorbide-5-isobutyrate: 18.6 g 2-allyl-isosorbide is stirred for 2 hours at 60° C. with 15.8 g isobutyric anhydride with addition of 0.1 g p-toluenesulfonic acid. Thereafter one distills in vacuo. B.p. (0.06): 107° C.

(b) 2-(2,3-epoxypropyl)-isosorbide-5-isobutyrate: Obtained as oily, crude product and further used in this form.

(c) 2-(2-hydroxy-3-isopropylaminopropyl)-isosorbide-5-isobutyrate: Oxalate: 0.25 $H_2O$: m.p. 100° C. (from ethanol), $[alpha]_D^{20}+53.4$ (c=0.861, $H_2O$).

EXAMPLE 17

2-(2-hydroxy-3-isopropylaminopropyl)-isosorbide-5-pivaloate (a) 2-allyl-isosorbide-5-pivaloate: 18.6 g 2-allyl-isosorbide, 12.0 g pivaloyl chloride and 25 ml pyridine are stirred in 100 ml dichloromethane for 30 minutes at room temperature. Thereafter one extracts with water and concentrates the methylene chloride phase. The residue is distilled in vacuo. B.p. (0.05): 106° C.

(b) 2-(2,3-epoxypropyl)-isosorbide-5-pivaloate: Obtained as an oily, crude product and further used in this form.

(c) 2-(2-hydroxy-3-isopropylaminopropyl)-isosorbide-5-pivaloate: Oxalate: m.p. 119°–121° C. (from acetone), $[alpha]_D^{20}+50.3$ (c=0.815, H$_2$O).

EXAMPLE 18

2-(2-hydroxy-3-isopropylaminopropyl)-isosorbide-5-caprinate (a) 2-(2,3-epoxypropyl)-isosorbide-5-caprinate: To a solution of 20.2 g (2-(2,3-epoxypropyl)-isosorbide (isomer with m.p. 88°–90° C., see Example 1) and 10 g pyridine in 50 ml dichloromethane is added dropwise at 0°–5° C. a solution of 19.0 g capric acid chloride in 50 ml dichloromethane. After 2 hours stirring at room temperature, one decomposes the mixture with water, separates the phases and concentrates the organic phase. The remaining oily residue is further reacted in this form.

(b) 2-(2-hydroxy-3-isopropylaminopropyl-isosorbide-5-caprinate: Oxalate: m.p. 113°–115° C. (from acetone, $[alpha]_D^{20}+30.6$ (c=1.177, H$_2$O).

EXAMPLE 19

2-(2-hydroxy-3-isopropylaminopropyl)-isosorbide-5-acetate (a) 2-(2,3-epoxypropyl)-isosorbide-5-acetate: Analogous to Example 18(a) from 2-(2,3-epoxypropyl)-isosorbide (isomer with m.p. 88°–90° C.) and acetyl chloride. B.p. (0.1): 128° C.

(b) 2-(2-hydroxy-3-isopropylaminopropyl)-isosorbide-5-acetate: Oxalate: m.p. 113°–114° C. (from ethanol), $[alpha]_D^{20}+50.6$ (c=1.018, methanol).

EXAMPLE 20

2-(2-hydroxy-3-isopropylaminopropyl)-isosorbide-5-undecylenate (a) 2-(2,3-epoxypropyl)-isosorbide-5-undecylenate: Analogous to Example 18(a) from 2-(2,3-epoxypropyl) isosorbide (isomer with m.p. 88°–90° C.) and undecylenyl chloride. Oily crude product.

(b) 2-(2-hydroxy-3-isopropylaminopropyl)-isosorbide-5-undecylenate: Oxalate: m.p. 111° C. (from acetone), $[alpha]_D^{20}+37.3$ (c=1.255, methanol).

EXAMPLE 21

2-[(2-hydroxy-3-(7-theophyllinyl)-propyl]-isosorbide 10.1 g 2-(2,3-epoxypropyl-isosorbide is boiled under reflux for 3 hours with 9.0 g theophyllin 150 ml 1-propanol with addition of 1 ml pyridine. Thereafter one concentrates the mixture in vacuo and dissolves the residue in water. One alkalizes with dilute aqueous sodium hydroxide solution, saturates with sodium chloride and extracts 5 times with 100 ml dichloromethane each time. The combined organic extracts are dried over Na$_2$SO$_4$ and concentrated in vacuo. The residue is recrystallized from ethanol. Yield: 12.4 g, m.p. 155°–156° C., $[alpha]_D^{20}+2.86$ (c=0.699, H$_2$O).

EXAMPLE 22

2-[2-hydroxy-3-(7-theophyllinyl) propyl]-isosorbide-5-nitrate

From 2-(2,3-epoxypropyl)-isosorbide-5-nitrate and theophyllin analogously to the preceding example. M.p. 145°–146° C. (from ethanol) $[alpha]_D^{20}+91.2$ (c=0.822, acetone).

EXAMPLE 23

5-[2-hydroxy-3-(7-theophyllinyl)-propyl]-isosorbide-2-nitrate

From 5-(2,3-epoxypropyl)-isosorbide-2-nitrate and theophyllin. M.p. 143°–144° C. (from 2-propanol), $[alpha]_D^{20}+39.3$ (c=0.788, acetone).

EXAMPLE 24

Bis-2,5[2-hydroxy-3-(7-theophyllinyl)-propyl]-isosorbide

From 2,5-bis(2,3-epoxypropyl)-isosorbide and theophyllin. The substance was obtained as colorless, amorphous powder containing 0.25 mole water. M.p. 155°–160° C. (decomposes) (from 2-propanol), $[alpha]_D^{20}+217.6$ (c=0.594, acetone).

EXAMPLE 25

2-[2-hydroxy-3-(1-theobrominyl)-propyl]-isosorbide
From 2-(2,3-epoxypropyl)-isosorbide and theobromine. M.p. 125°–127° C. (from 2-propanol), $[alpha]_D^{20}+27.0$ (c=0.629, methanol).

EXAMPLE 26

5-[3-[N-benzyl-N-(7-theophyllinyl)-ethylamino)]-2-hydroxypropyl]-isosorbide 0.1 mole 7-(2-benzylaminoethyl)-theophyllin (DAS 1,011,424) and 0.1 mole 5-(2,3-epoxypropyl)-isosorbide are heated in 300 ml ethanol for 20 hours under reflux. On cooling to 0° C., the reaction product crystallizes out. The product is suction-filtered and recrystallized from methanol. Yield: 68% theoretical, m.p. 150°–151° C., $[alpha]_D^{20}+38.5$ (c=0.818, methanol).

EXAMPLE 27

2-[3-[N-benzyl-N-(2-(7-theophyllinyl)-ethylamino)]-2-hydroxypropyl]-isosorbide From
7-(2-benzylaminoethyl)-theophyllin and
2-(2,3-epoxypropyl)-isosorbide analogously to the preceding example. Hydrochloride . 0.5 H$_2$O: sinters above 88°–94° C. (from acetone), $[alpha]_D^{20}+14.8$ (c=0.88, methanol).

EXAMPLE 28

5-[3-[2-(7-theophyllinyl)-ethylamino]-2-hydroxypropyl]-isosorbide 10.3 g 5-[3-N-benzyl-N-(2-(7-theophyllinyl)-ethylamino)]-2-hydroxypropyl]-isosorbide (Example 26) is dissolved in 100 ml 80% methanol, mixed with 2 g 5% Pd/C and hydrogenated at room temperature until hydrogen absorption ceases. The material is filtered from the catalyst and the filtrate is concentrated. The residue is dissolved in methanol and the hydrochloride is precipitated with etheral HCl. After recrystallization from 2-propanol, the desired product is obtained as the hydrochloride, in 79% yield, in the form of colorless crystals which begin to sinter above 82°–86° C. $[alpha]_D^{20}+32.3$ (c=0.743, methanol).

EXAMPLE 29

5-[3-[N-benzyl-N-(2-(7-theophyllinyl)-ethylamino]-2-hydroxl]-isosorbide-2-nitrate From 7-(2-benzylaminoethyl)-theophyllin and 5-(2,3-epoxypropyl)-isosorbide-2-nitrate. Hydrochloride . 0.25 H$_2$O: sinters above 82°–87° C. (from 2-propanol), $[alpha]_D^{20}+32.8$ (c=0.883, methanol).

EXAMPLE 30

2-[3-[N-benzyl-N-(3-(7-theophyllinyl)-propylamino]-2-hydroxypropyl-isosorbide

From 7-(3-benzylaminopropyl)-theophyllin [Chem. Ber. 90, 1651 (1957)] and 2-(2,3-epoxypropyl-isosorbide. Hydrochloride . 0.5 H$_2$O: sinters above 85°–90° C. (from 2-propanol), $[alpha]_D^{20}+15.5$ (c=1.097, methanol).

EXAMPLE 31

2-[3-[3-(7-theophyllinyl)-propylamino]-2-hydroxypropyl)-isosorbide

From 2-([3-[N-benzyl-N-(3-(7-theophyllinyl)propylamino)]-2-hydroxypropyl]-isosorbide (Example 30) by catalytic hydrogenation with Pd/C. Hydrochloride sinters above 162°–165° C. (from ethanol), $[alpha]_D^{20}+13.1$ (c=0.648, methanol).

EXAMPLE 32

2-[3-(7-theophyllinyl)-ethylamino]-2-hydroxypropyl]-isosorbide

From 2-([3-[N-benzyl-N-(2-(7-theophyllinyl)-ethylamino)]-2-hydroxypropyl]-isosorbide (Example 27) by catalytic hydrogenation. Hydrochloride . 0.5 H$_2$O: sinters above 98°–100° C. (from ethanol), $[alpha]_D^{20}+20.3$ (c=0.885, methanol).

EXAMPLE 33

2-[3-[N-benzyl-N-(2-(7-theophyllinyl(-propylamino]-2-hydroxypropyl]-isosorbide-5-nitrate From 7-(3-benzylaminopropyl)-theophyllin and 2-(2,3-epoxypropyl)-isosorbide-5-nitrate. Hydrochloride . 0.5 H$_2$O: sinters above 98°–102° C. (from 2-propanol), $[alpha]_D^{20}+54.4$ (c=1.076, methanol).

EXAMPLE 34

2-[3-[N-benzyl-N-(3-(7-theophyllinyl)-propylamino]-2hydroxypropyl]-isomannide

From 7-(3-benzylaminopropyl-theophyllin and 2-(2,3-epoxypropyl)-isomannide. Hydrochloride . H$_2$O: sinters above 94°–97° C. (from 2-propanol), $[alpha]_D^{20}+42.6$ (c=0.716, methanol).

EXAMPLE 35

2-[3-[3-(7-theophyllinyl)-propylamino]-2-hydroxypropyl-isomannide

From the compound described in Example 34 by catalytic hydrogenation. Hydrochloride . 0.75 H$_2$O: sinters above 143°–153° C. (from 2-propanol), $[alpha]_D^{20}+54.9$ (c=0.784, methanol).

EXAMPLE 36

5-[3-[2-(7-theophyllinyl)-ethylamino]-2-hydroxypropanol]-isosorbide-2-nitrate

From 7-(2-aminoethyl)-theophyllin (DAS 1,011,424) and 5-(2,3-epoxypropyl)-isosorbide-2-nitrate. Hydrochloride . 0.25 H$_2$O: sinters above 76°–80° C. (from 2-propanol), $[alpha]_D^{20}+37.0$ (c=0.81, methanol).

EXAMPLE 37

2-[3-[3-(7-theophyllinyl)-propylamino]-2-hydroxypropyl]-isosorbide-5-nitrate

From 7-(3-aminopropyl)-theophyllin [(Collect. Czech. Chem. Commun. 38, 1571 (1973)] and 2-(2,3-epoxypropyl)-isosorbide-5-nitrate. Hydrochloride . 0.5 H$_2$O: sinters above 83°–86° C. (from 2-propanol), $[alpha]_D^{20}+63.1$ (c=0.919, methanol).

EXAMPLE 38

2-[3-(N$^6$-benzoyl-9-adenyl)-2-hydroxypropyl]-isosorbide

From N$^6$-benzoyl-ademine and 2-(2,3-epoxypropyl)isosorbide. M.p. 168°–169° C. (from ethanol/ethyl acetate), $[alpha]_D^{20}+20.0$ (c=0.801, methanol).

EXAMPLE 39

2-[3-(9-adenyl)-2-hydroxypropyl]-isosorbide

From the compound described in Example 38 by splitting off the benzoyl group with sodium methylate in methanol solution. The substance crystallizes out of ethanol with 0.25 mole water. M.p. 172°–175° C., $[alpha]_D^{20}+24.0$ (c=0.811, H$_2$O).

EXAMPLE 40

Bis-2,5-[3-[N-benzyl-N-(2-(7-theophyllinyl)-ethyl)-amino]-2-hydroxypropyl]-isomannide From 7-(2-benzylaminoethyl)-theophyllin and 2,5-bis-(2,3-epoxypropyl)-isomannide. Dihydrochloride . 0.5 H$_2$O: sinters above 146°–148° C. (from 2-propanol), $[alpha]_D^{20}+44.7$ (c=0.795, methanol).

EXAMPLE 41

Bis-2,5-[2-(7-theophyllinyl-ethylamino]-2-hydroxypropy-1-isomannide;

From the preceding compound (Example 40) by catalytic hydrogenation. Dihydrochloride . H$_2$O: sinters above 127°–132° C. (from ethanol), $[alpha]_D^{20}+51.8$ (c=0.733, methanol).

EXAMPLE 42

2-[3-(9-(6-methylmercaptopurinyl)-2-hydroxypropyl]-isosorbide is formed from 2-(2,3-epoxypropyl)isosorbide and 6-methyl-mercaptopurine; sinters at 55°–60° C. (from toluene); $[alpha]_D^{20}+12.8$ (c=0.98, methanol).

We claim:

1. A dianhydrohexite derivative having the Formula I

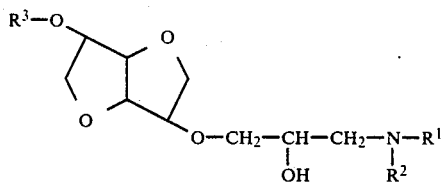

wherein:
$R^1$ is hydrogen or a benzyl group;
$R_2$ is an alkyl group having 1–4 carbon atoms; and
$R^3$ is hydrogen, a straight or branched, saturated or unsaturated carboxylic acid radical having 1 to 20 carbon atoms, a pyridylcarbonyl group, an $NO_2$ group or a group having the formula

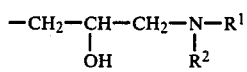

wherein $R^1$ and $R^2$ are as hereinbefore defined; and acid addition salts thereof.

2. A 1,4:3,6-dianhydrohexite derivative according to claim 1, characterized in that the derivative is one of 1,4:3,6-dianhydro-L-idite having the Formula II

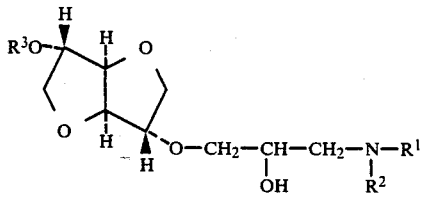

where $R_1$, $R^2$ and $R^3$ are as defined in claim 1; and acid-addition salts thereof.

3. A 1,4:3,6-dianhydrohexite derivative according to claim 1, characterized in that the derivative is one of 1,4:3,6-dianhydro-D-glucite having the formulae III and IV

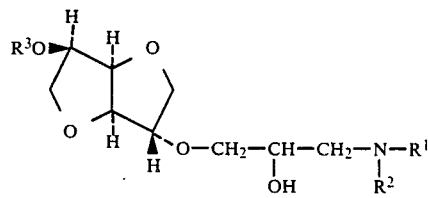

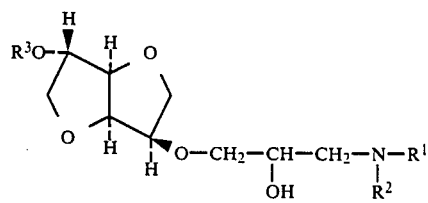

in which $R^1$, $R^2$ and $R^3$ are as defined in claim 1; and acid-addition salts thereof.

4. A 1,4:3,6-dianhydrohexite derivative according to claim 1, characterized in that the derivative is one of 1,4:3,6-dianhydro-D-mannite having the Formula V

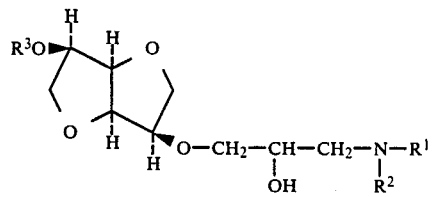

in which $R^1$, $R^2$ and $R^3$ are as defined in claim 1; and acid-addition salts thereof.

5. A pharmaceutical composition for the treatment of a heart or circulatory disease which comprises a compound of formula I as defined in claim 1 or a pharmaceutically acceptable acid-addition salt thereof in an amount effect in the treatment of a heart or a circulatory disease, and a pharmaceutically acceptable carrier.

* * * * *